United States Patent [19]
Redikultsev et al.

[11] 4,276,264

[45] Jun. 30, 1981

[54] DEVICE FOR STERILIZING LIQUID MEDIA BY STEAM

[76] Inventors: Jury V. Redikultsev, mikroraion "G", dom 19, kv. 113; Alexandr N. Shkidchenko, mikroraion "G", dom 30, 51; Oleg P. Gorbunov, mikroraion "V", dom 28, kv. 18; Leonid A. Litvinenko, mikroraion "AB", dom 8, kv. 74, all of Puschino Moskovskoi oblasti, U.S.S.R.

[21] Appl. No.: 133,842

[22] Filed: Mar. 25, 1980

[51] Int. Cl.$^3$ .............................................. A61L 2/06
[52] U.S. Cl. ...................................... 422/307; 422/26
[58] Field of Search ................. 422/26, 307, 299, 243, 422/230, 231

[56] References Cited

U.S. PATENT DOCUMENTS

| | | | |
|---|---|---|---|
| 1,998,679 | 4/1935 | Linde | 422/307 X |
| 2,917,372 | 12/1959 | Wallin | 422/231 X |
| 3,687,612 | 8/1972 | Ernst | 422/27 |
| 4,160,002 | 7/1979 | Janovtchik | 422/307 X |

FOREIGN PATENT DOCUMENTS

| | | | |
|---|---|---|---|
| 160092 | 10/1953 | Australia | 422/26 |
| 268883 | 7/1968 | U.S.S.R. | 422/26 |

*Primary Examiner*—Barry Richman

[57] ABSTRACT

A device for sterilizing water-containing liquid media by steam comprises a sterilizing vessel with inlet and outlet connections for processed liquid media. A heater is provided in the lower portion of the vessel, while a condenser is arranged in the upper portion thereof. The vessel also houses a coaxially mounted steam-transfer unit representing gas-lift tube with a diffuser disposed over the heater.

1 Claim, 1 Drawing Figure

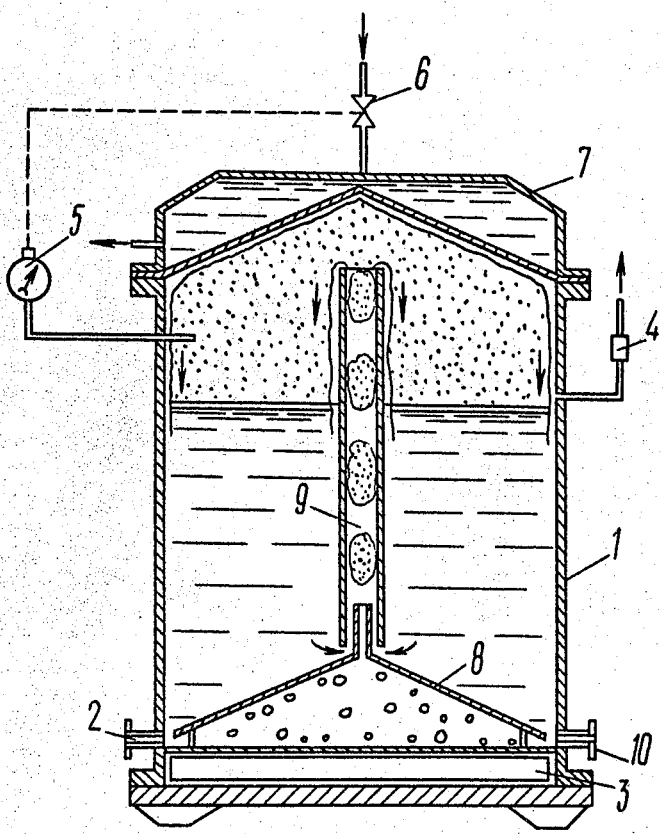

4,276,264

DEVICE FOR STERILIZING LIQUID MEDIA BY STEAM

FIELD OF THE INVENTION

The present invention relates to microbiology and in particular to devices for sterilizing water-containing liquid media by steam. The invention may be used in medical, microbiological and food industries. It is also suitable for research applications.

PRIOR ART

Liquid media are generally sterilized by live steam using injectors, bubblee flasks, pressure tubes and also various columns and chambers. Extensive use is made at present of autoclaves for live-steam sterilization under pressure (cf. J. Meynell and E. Meynell "Experimental Microbiology", "Mir" publishers, Moscow, 1967, p. 119).

The aforesaid sterilization devices are either unfit for sterilizing circulating liquid media or entail an intricate operating procedure due to frequent dismantling, cleaning and acid treatment associated with the need to remove deposit from the interior of the walls, a limitation substantially decreasing their effectiveness.

Also known in the art is a device for sterilizing liquid media by steam, which represents a column comprising a sterilizing vessel with a coaxially mounted steam-transfer unit and inlet and outlet connections (cf. "Production of Antibiotics", "Meditsina" publishers, Moscow, 1970, p. 89).

In the aforesaid sterilizing column operating from an external steam generator the liquid medium is diluted to 10-20% of the initial volume in sterilization. In such a sterilizing column the sterilized medium may not be held under specified conditions, a disadvantage necessitating the utilization of an additional holding facility.

SUMMARY OF THE INVENTION

It is an object of the present invention to provide a device for sterilizing water-containing liquid media by steam generated from said liquid media, which permits a complete sterilization cycle without any change in the initial volume of a sterilized medium.

Another object of the invention is to provide a device enabling a sterilized medium to be held in the entire volume of a sterilizing vessel.

The foregoing objects are accomplished by that in a device for sterilizing liquid media by steam comprising a sterilizing vessel with a coaxially mounted steam transfer unit and inlet and outlet connections, according to the invention, the sterilizing vessel is provided with a heating element disposed in its lower portion and a condenser arranged in the upper portion thereof, while the steam-transfer unit represents an air-lift tube with a diffuser arranged over the heating element.

The device for sterilizing liquid media by steam forming the subject of the present invention permits a complete sterilization cycle in a single volume without any change in the initial volume of a sterilized medium and use of periodic sterilization within the system.

BRIEF DESCRIPTION OF DRAWING

The invention will now be described with reference to a specific embodiment thereof, taken in conjunction with the accompanying drawing which is a longitudinal sectional view of a device for sterilizing liquid media by steam according to the invention.

DETAILED DESCRIPTION OF THE INVENTION

Referring to the drawing the device for sterilizing water-containing liquid media by steam generated from said liquids media forming the subject of the present invention comprises a cylindrical sterilizing vessel 1 containing a sterilized object and designed for accomplishing a properly sterilization process. The sterilizing vessel 1 has an inlet connection 2 with a shut-off arrangement (not shown in the drawing) through which the sterilizing vessel 1 is filled with initial medium, said vessel being hermetically sealed thereafter. The hereinproposed device also includes a heating element 3 made to correspond to the cross-section of the sterilizing vessel 1 to provide for a developed thermal radiation surface, said heating element being arranged in the lower portion of the sterilizing vessel 1. A tapered diffuser 8 has a base diameter somewhat smaller than the inner diameter of the sterilizing vessel 1 and is installed over the heating element 3 within a short distance therefrom to allow free passage of the processed medium to the surface of the heating element 3 and its evaporation under the tapered portion of the diffuser 8. The diffuser 8 terminates in a nozzle representing a tube rigidly secured at the top of the tapered portion of the diffuser 8 along the central axis thereof and facilitating steam discharge from the diffuser 8. Secured on the free end of the nozzle is gas-lift tube 9 acting as gas-lift pump (injector) to enable inflow of the steam and processed liquid medium in sterilization.

Mounted in the upper portion of the sterilizing vessel 1 is a condenser 7 representing a hollow structure with a sunk base to increase a steam condensation surface and enable its delivery to the internal walls of the sterilizing vessel 1. Moreover, such arrangement of the condenser 7 permits obtaining the temperature gradient in the sterilizing vessel 1 while said vessel 1 is used to sustain sterilization, a feature appreciably reducing the sterilized liquid medium exposure time and allowing the destruction of spore (pathogenic) microorganisms.

An electrocontact pressure gauge 5 arranged in the upper portion of the vessel 1 performs the dual function of setting a sterilization pressure and providing pressure readings in obtaining stabilized operating conditions. To adjust the flow of coolant through the condenser 7 during pressure stabilization in the sterilizing vessel 1 provision is made for a shutter 6. The shutter 6 operates as an electric pulse is applied thereto from the electrocontact pressure gauge 5. An outlet connection 10 provided with a shut-off arrangement (not shown in the drawing) is arranged in the lower portion of the sterilizing vessel 1 and permits drainage of the sterilized medium into a suitable receiving vessel or fermenter (not shown in the drawing).

A safety valve 4 ensures safe operation of the device.

The operation of the hereinproposed device for sterilizing liquid media by steam is based on a constant flow of the liquid medium through the gas-lift tube 9 under the action of steam with a predetermined pressure maintained in the sterilizing vessel 1, the entire work procedure being accomplished in two stages. During the first stage, the air is removed from the sterilizing vessel 1. The steps involved are hemetic sealing of the sterilizing vessel 1, disconnection of the electrocontact pressure gauge 5, and connection of the heating element 3. Consequently, the pressure inside the sterilizing vessel 1 increases and the air is released through the safety valve 4. The subsequent steps are disconnection of the heating element 3 and connection of the electrocontact pressure gauge 5. An electric pulse from said electrocontact gauge opens the shutter 6 allowing the coolant to come to the condenser 7 whereby the sterilizing vessel 1 will be cooled. The cooled sterilizing vessel 1 is free of air, has a decreased pressure and may now be loaded with a liquid medium to be sterilized. The second stage (sterilization of the processed medium) may thus begin.

With the connection 2 open, the sterilizing vessel 1 is filled with the liquid medium avoiding the ingress of air. After the connection 2 is closed, the movable contact of the electrocontact pressure gauge 5 is adjusted for a pressure corresponding to the desired liquid medium sterilization temperature. Thereafter the heating element 3 is connected and the medium temperature is increased to its vaporization point whereby the pressure within the sterilizing vessel 1 will be increased. As it reaches the value set on the electrocontact pressure gauge 5, an electric pulse from said pressure gauge 5 is fed to the shutter 6, thus enabling the passage of the coolant to the condenser 7. The temperature gradient is set up in the sterilizing vessel 1 whereby the assigned liquid medium sterilization pressure will be stabilized and the process of killing microorganisms will be intensified accordingly.

The heating element 3 remains connected throughout the procedure so that the medium vapours concentrated under the diffuser 8 are discharged at a high rate through the nozzle to the gas-lift tube 9 causing the inflow of the sterilized medium and its upward movement over the tube 9. The sterilized medium leaving the gas-lift tube 9 is drained downwards into the initial space, while the steam is delivered to the cooled surface of the condenser 7 wherein the condensation occurs and the water is also drained into the initial space, which restores the concentration of the sterilized medium. The sterilized medium will thus be vigorously stirred.

Upon completion of sterilization, the heating is stopped by disconnecting the heating element 3 and the sterile medium is drained through the connection 10, said connection being shut off after drainage. The empty sterilizing vessel 1 is then cooled after which it may be loaded with a fresh liquid medium.

The device forming the subject of the present invention does not call for the utilization of any additional amount of water for steam generation, an advantage providing a constant concentration of liquid medium in sterilization. Another feature of the invention is that the sterilized medium is recirculated in a single volume within any time period desired whereby the use of an additional holding facility is avoided. Furthermore, the destruction of microflora is intensified due to the temperature gradient, an advantage allowing the killing of various pathogenic and spore-forming microorganisms. Also, the operational accuracy is enhanced due to stabilized pressure in liquid medium sterilization.

What is claimed is:

1. A device for sterilizing water-containing liquid media by steam comprising a sterilizing vessel; an inlet connection for said liquid media communicating with said sterilizing vessel; an outlet connection for said liquid media communicating with said sterilizing vessel; a heater disposed in the lower portion of said sterilizing vessel; a condenser arranged in the upper portion of said sterilizing vessel; a diffuser located in said vessel over said heater; and a gas-lift tube coaxially mounted within said sterilizing vessel and communicating with said diffuser on one end thereof.

* * * * *